(12) United States Patent
Vargas (10) Patent No.: US 10,709,316 B2
(45) Date of Patent: Jul. 14, 2020

(54) METHOD AND APPARATUS FOR A ROTATING SLEEVE FOR ENDOSCOPIC PROPULSION WITH MITIGATION OF COLONOSCOPIC PERFORATION

(71) Applicant: Eladio A. Vargas, Glenview, IL (US)

(72) Inventor: Eladio A. Vargas, Glenview, IL (US)

(73) Assignee: Eladio A. Vargas, Glenview, IL (US)

( * ) Notice: Subject to any disclaimer, the term of this patent is extended or adjusted under 35 U.S.C. 154(b) by 0 days.

(21) Appl. No.: 15/615,627

(22) Filed: Jun. 6, 2017

(65) Prior Publication Data

US 2019/0125169 A1    May 2, 2019

(51) Int. Cl.
*A61B 1/00* (2006.01)
*A61B 1/31* (2006.01)
*A61B 1/01* (2006.01)

(52) U.S. Cl.
CPC ........ *A61B 1/00135* (2013.01); *A61B 1/0016* (2013.01); *A61B 1/00071* (2013.01); *A61B 1/00128* (2013.01); *A61B 1/00133* (2013.01); *A61B 1/00154* (2013.01); *A61B 1/00156* (2013.01); *A61B 1/01* (2013.01); *A61B 1/31* (2013.01)

(58) Field of Classification Search
CPC ............ A61B 1/00128; A61B 1/00133; A61B 1/00154; A61B 1/00156; A61B 1/0016; A61B 1/001; A61B 1/00105; A61B 1/00121; A61B 1/00135; A61B 1/016
See application file for complete search history.

(56) References Cited

U.S. PATENT DOCUMENTS

| 4,740,058 | A | * | 4/1988 | Hori | ........... | G03B 17/48 |
| | | | | | | 285/399 |
| 2001/0037050 | A1 | * | 11/2001 | Lemperle | ...... | A61B 1/00105 |
| | | | | | | 600/135 |

(Continued)

*Primary Examiner* — Aaron B Fairchild
(74) *Attorney, Agent, or Firm* — Patent Ventures, LLC (57) ABSTRACT

The present invention discloses an endoscopic sleeve apparatus for mitigating propulsion-related epithelial tearing, said apparatus comprising: an elastomeric, pliable, and rotatable sleeve for encasing an elongated shaft member of an endoscope; any one of a right-turn or left-turn helical threading disposed on the outer surface of the sleeve from a proximal base of the endoscope and radially extending to a distal tip of the endoscope; a distal tip port opening configured for allowing at least one channel and, or lumen axially disposed within the elongated shaft member of the endoscope to be engaged to the distal tip port opening for release and, or capture of any agent; a proximal end housing comprising at least one motor coupled to at least one actuator gear, whereby said actuator is in operable communication to the rotatable sleeve via a sleeve-actuator junction seal; a finger-led control disposed on a surface of the proximal end housing and operably coupled to the motor and, or actuator gear for triggering rotational force; and wherein the rotational force caused by the motor and, or actuator gear drives axial rotation of the rotatable sleeve over the elongated shaft member of the endoscope via the sleeve-actuator junction seal, and thereby allowing for forward propulsion of the endoscope with epithelial tearing risk mitigation.

16 Claims, 7 Drawing Sheets

(56) References Cited

U.S. PATENT DOCUMENTS

| | | | | |
|---|---|---|---|---|
| 2005/0272976 A1* | 12/2005 | Tanaka | ............... | A61B 1/00158 600/114 |
| 2008/0262305 A1* | 10/2008 | Omoto | ............... | A61B 1/00154 600/118 |
| 2011/0319713 A1* | 12/2011 | Frassica | ............. | A61B 1/00154 600/114 |
| 2012/0029281 A1* | 2/2012 | Frassica | ............. | A61B 1/00156 600/114 |
| 2013/0035552 A1* | 2/2013 | Moriyama | ......... | A61B 1/00154 600/149 |
| 2014/0296771 A1* | 10/2014 | Naito | ................. | A61B 1/00156 604/19 |
| 2015/0196191 A1* | 7/2015 | Naito | ................. | A61B 1/00156 600/114 |
| 2017/0059009 A1* | 3/2017 | Ishizaki | ............... | A61B 1/0016 |
| 2017/0273546 A1* | 9/2017 | Ishizaki | ............. | A61B 1/00135 |

* cited by examiner

METHOD AND APPARATUS FOR A ROTATING SLEEVE FOR ENDOSCOPIC PROPULSION WITH MITIGATION OF COLONOSCOPIC PERFORATION

BACKGROUND OF THE INVENTION

Field of Invention

The field of invention relates to an endoscopic sleeve, more particularly, to a sleeve slidably disposed over an endoscope and further coupled to a power unit/actuator gear encased in a snap-on housing and a sleeve-actuator junction seal for causing rotation of the sleeve, further mitigating the risk of epithelial tearing and trauma during interventional procedures.

Related Art

Epithelial tearing during endoscopic procedures, such as colonospic perforations (cp) is a growing risk. Epithelial, tissue, and organ trauma is, likewise, a growing risk of endoscopic procedures. Currently, incidence rates of tearing and, or trauma are as high as 5% of patients who have undergone colonoscopies. World J. Gastroenterol. 2010 Jan. 28; 16(4): 425-430. Current approaches revolve around ex facto management, such as antibiotic administration, and, or more aggressive approaches, such as open and, or laparoscopic treatment. Further complications may ensue from the original cp and subsequent procedures, namely post-polypectomy bleeding, diverticulitis, intraperitoneal hemorrhage, and colonic perforation. Worse yet, the cp and subsequent procedures may lead to the dreaded peritonitis, which is an inflammation of the membrane that lines the abdominal cavity. It usually occurs when either any one of bile, bacteria, stomach acid, partially digested food, and, or stool traverses via the aperture or perforation. Needless to say, cp-induced peritonitis is a deadly condition with a very poor prognosis. These ex facto approaches—with variable outcomes and potential complications—all place greater time and cost burdens on the patient and the overall health care system.

As a result, there has been a growing shift to preventive measures, as opposed to the ex facto approaches. One such preventive measure is an awareness of the sigmoid colon as being the main site of cp and having a low threshold for looping of the sigmoid colon. In other words, once a low looping threshold is recognized, then deciding against a colonoscopic procedure due to the increased risk for cp. Alternatively, performing a colonoscopy with total avoidance or careful engagement of the sigmoid colon may mitigate the risks of cp.

Non-invasive approaches, namely virtual colonoscopies, which reconstruct 2D or 3D imagery from MR and CT scans, obviously avoid the risk of cp. However, there are significant limitations, not the least of which is the fact that any detected polyps or tumors may not be removed. What's more, virtual methods do not allow the clinician to detect polyps/lesions smaller than 5 mm. As a result, although non-invasive and cp avoiding, oversight of micro polyps/tumors is a significant issue with the various virtual methods.

As far as endoscopic accessories in the market that mitigate cp, the DiLumen endoluminal interventional sleeve fits securely over any endoscopic sleeve and deploys a series of balloons to stabilize the endoscope once the distal tip of the scope is situated over the target site. While it mitigates the risk of cp during endoscopic manipulation over a target site, it doesn't address the risk of cp during forward propulsion to the target site and, or reverse propulsion for endoscopic withdrawal.

CP-mitigating endoscopic/sleeves disclosed in the prior art, likewise, do not address the issue of mitigating cp during propulsion. Much of the art discloses rotation of the elongated shaft of the endoscope, or a slidably disposed sleeve that is not rotatable. Subsequently, both endoscopic propulsion and cp mitigation are not both simultaneously achievable. Axon, et al. (U.S. Pat. No. 6,293,907 B1) discloses an endoscopic cover having a wedge-shaped protrusion configured such that the frictional resistance is greater upon rearward displacement, as opposed to forward displacement. The Axon sleeve does not disclose for a helical threading facilitating a forward and, or reverse propulsion, along with not disclosing any features facilitating cp-risk mitigation.

According to Bern, et al. (US 20150297060 A1), a propulsion system that may be retro-fitted onto any one of a body cavity searching device is provided. Bern discloses a drive shaft or transmission, converting the rotational energy into shaft rotation for longitudinal movement by way of a rotatable rod or band. Secondly, the rotatable surface is further disposed with a balloon-belt arrangement, whereby inflation of the balloon adheres the belts for causing forward propulsion. While Bern does describe a propulsive system—albeit in a complex and convoluted manner—it does not disclose a system in which cp risk is mitigated. In fact, it discloses for the contrary; the extensive rod-balloon-belt system for propulsion increases the width and, or rigidity of the propulsive system, thereby effectively voiding any cp mitigation benefits.

As a result, a serious void in the market and prior art exists for an endoscopic propulsion system with significant cp risk mitigation. Extant devices and systems do not address these concerns; they each either disclose novel improvements for endoscopic propulsion or cp-risk mitigation—but not both. Moreover, none of the extant references disclose for a rotatable sleeve that is rod-free and simply fits over the shaft of an endoscope, further disposed with helical threading to enhance propulsion in either direction. There is a significant need for a propulsive device that is shaft-free or rod-free rotatable that engages the lumen surface with an inconspicuous helical threading—as opposed to a cumbersome protrusion or belt/inflatable balloon assembly.

SUMMARY

The present invention addresses these limitations by disclosing features critical to providing propulsive aid to an endoscope, while simultaneously mitigating the risk of cp and, or trauma during endoscopic procedures—including, but not limited to, colonoscopies. The present invention addresses these twin limitations by disclosing a rotatable sleeve with helical threading that is coupled to a rotational force output via a junction seal—and free of a rotatable rod, drive unit, inflatable balloon or inflatable balloon/belt assembly. As a result, the shaft-free or rod-free axial rotation of the helical-threaded sleeve, causing propulsion does not increase the risk of cp, but rather, mitigates it due to the lack of rigidity, and due to the lack of clunky protrusions and balloon/belt assemblies. Patient outcomes with respect to interventional procedures will exponentially improve from the reduced risk of cp. Moreover, due to the lowered risk of complications and pain/discomfort, patients may undergo such procedures with lower sedation and monitoring in the confines of a clinician's office, rather than in more expensive and time-consuming centers, such as outpatient clinics, etc. Not only will patient outcomes improve, but the present invention will put downward pressure on time and cost burdens to the overall healthcare system.

It is an object of the invention to disclose an endoscopic sleeve apparatus for mitigating propulsion-related epithelial tearing comprising: an elastomeric, pliable, and rotatable sleeve for encasing an elongated shaft member of an endoscope; any one of a right-turn or left-turn helical threading disposed on the outer surface sleeve from a proximal base of the endoscope and radially extending to a distal tip axially disposed within the elongated shaft member of the endoscope to be engaged to the distal tip port opening for release and, or capture of any agent; a proximal end housing comprising: at least one motor coupled to at least one actuator gear, whereby the actuator is in operable communication to the rotatable sleeve via a sleeve-actuator junction seal; a finger-led control disposed on a surface of the proximal end housing and operably coupled to the motor and, or actuator gear for triggering rotational force; and rotation of the rotatable sleeve over the elongated shaft member of the endoscope via the endoscope with epithelial tearing risk mitigation. In one aspect of the invention, the apparatus may be configured to operate under any one of, or combination of, a control circuitry, control module, control unit, and, or control operator of any one of, or combination of, the apparatus, and, or the underlying endoscope. In accordance with an aspect, the apparatus may be slidably disposed or snapped-on the base of a tubular member of any one of a flexible or rigid scope, wherein the scope is configured to release any agent from any channel or lumen of the scope; capture any image from a fiber optic line from a second channel or lumen; and protracting a loop to capture or extract a polyp from a third channel or lumen. The distal tip of any one of, or combination of, an apparatus, and, or a scope, may further comprise a ultra-sound probe, or any other detection guide for confirmation of location of any one of a tumor, polyp, and, or lesion.

In yet another object of the invention, a method for mitigating propulsion-related epithelial tearing is provided, said method comprising steps of: threading an outer surface of a rotatable sleeve encasing an elongated shaft member of an endoscope, from a proximal base of the endoscope and radially extending to a distal tip of the endoscope; coupling at least one motor to at least one actuator gear, whereby the actuator gear is in operable communication to the rotatable sleeve via a sleeve-actuator junction seal; triggering rotational force by a finger-led control disposed on a surface of the proximal end housing and operably coupled to the motor and, or actuator gear; and rotation of the rotatable sleeve over the elongated shaft member of the endoscope.

Other aspects and advantages of the invention will be apparent from the following description and the appended claims. Other applications: small bowel scoping with a smaller diameter scope; snaring a lumen for polyps/lesions; and releasing air/water for lumen clearance, all may be coupled to the sleeve/housing apparatus to facilitate propulsion with cp mitigation. It is to be understood that the foregoing general description and the following detailed description are exemplary and explanatory only, and are not necessarily restrictive of the disclosure. The accompanying drawings, which are incorporated in and constitute a part of the specification, illustrate subject matter of the disclosure and together with the general description, serve to explain the principles of the present disclosure. The disclosure will be understood by those skilled in the art from the following detailed description and drawings.

BRIEF DESCRIPTION OF DRAWINGS

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which.

DETAILED DESCRIPTION OF DRAWINGS

Figure 1:
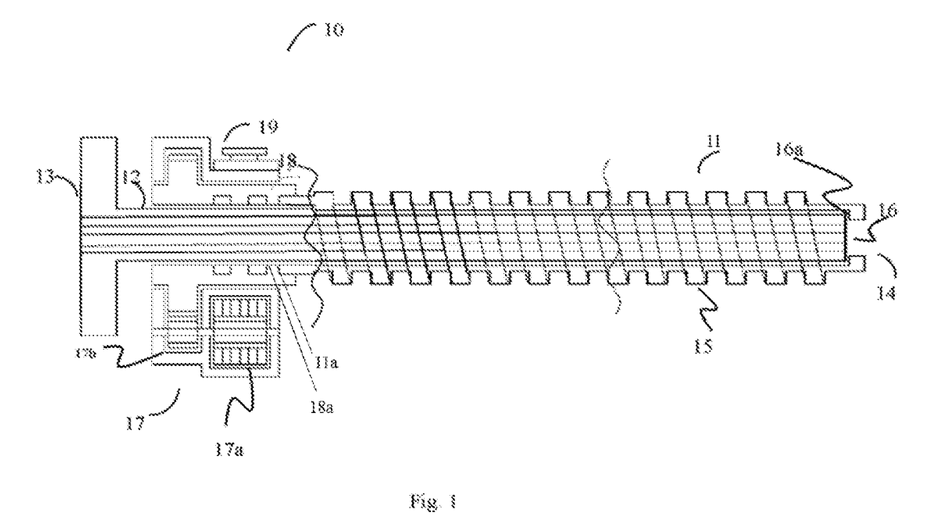
FIG. 1 is a side elevational view of the rotatable sleeve apparatus coupled to the rotational force output housing disposed on a scope according to an aspect of the invention.

The present disclosure describes embodiments of an apparatus and methods in which an endoscopic sleeve/rotational output housing itself or as part of an endoscope may be utilized to drive propulsion during an endoscopic procedure. FIG. 1 illustrates a side elevational view of the endoscopic propulsion and cp-risk mitigation apparatus, particularly the rotatable sleeve coupled to a sleeve-actuator junction seal and rotational output housing—disposed over any one of an existing standard endoscope used for interventional procedures, namely a colonoscopy. In one particular embodiment, the apparatus comprises an elastomeric, pliable, and rotatable sleeve 11 for encasing an elongated shaft member 12 of an endoscope; any one of a right-turn or left-turn helical threading 15 disposed on the outer surface of the sleeve from a proximal base 13 of the endoscope and radially extending to a distal tip 14 of the endoscope; a distal tip port opening 16 configured for allowing at least one channel and, or lumen axially disposed within the elongated shaft member 12 of the endoscope to be engaged to the distal tip port opening 16 for release and, or capture of any agent. Furthermore, a proximal end housing 17 may comprise: at least one motor 17a coupled to at least one actuator gear 17b, whereby said actuator 17b is in operable communication to the rotatable sleeve 11 via a sleeve-actuator junction seal 18; a finger-led control 19 disposed on a surface of the proximal end housing 17 and operably coupled to the motor 17a and, or actuator gear 17b for triggering rotational force. Finally, the rotational force caused by the motor 17a and, or actuator gear 17b drives axial rotation of the rotatable sleeve 11 over the elongated shaft member 12 of the endoscope via the sleeve-actuator junction seal 18, and thereby allowing for forward propulsion of the endoscope with epithelial tearing risk mitigation.

In another embodiment, in continuing reference to FIG. 1, the rotatable sleeve 11 may be comprised of any pliable, elastomeric, thermoplastic material that is surgical grade. Examples of such material are, but not limited to, silicone rubber, thermoplastic elastomer, latex, polyurethane, polyisoprene, nitrile sheath, etc. Critical characteristics include, but are not limited to, a high break point; wide biocompatibility; high elasticity; high tensile strength; wide operating environment compatibility; environmental resistance; autoclave sterilization resistance; wide thickness range (0.03 mm-0.5 mm), etc. The representative materials may be resistant to friction during rotation over the elongated shaft 12 of the endoscope. The representative material may also maintain a low coefficient of friction or lower its coefficient of friction upon an application of lubricant between the surface of the sleeve 11 and the surface of the elongated shaft 12 of the endoscope. The application of lubricant between surfaces may improve the axial rotation of the sleeve 11, thereby improving the propulsive force and further mitigate the risk of cp. Additionally, the low coefficient of friction of the sleeve 11 material—with the aid of a lubricant—enables the sleeve 11 to uniformly rotate over the surface of the elongated shaft 12 of the scope, without snagging or kinking.

Still in reference to FIG. 1, the distal tip port opening 16 further comprises a lip or overhang 16a to prevent the sleeve 11 from slipping off the elongated shaft 12 of the endoscope. The overhang 16a may have any range of size, limited to at least the size of a port opening 16 configured to allow ingress-egress of at least one working channel. In a preferred embodiment, the overhang 16a may be configured to allow exposure for a port opening 16 configured for at least three or four channels: fiber optic camera cable, polyp removal loop, suction, and, or water/agent delivery. In alternative embodiments, the overhang 16a may be pitched, rather than perpendicular from the remaining lateral portion of the tubular sleeve. This pitch of the overhang 16a may allow for a greater exposure of the distal tip port opening 16.

As shown by the bold, wavy lines in FIG. 1, the distal tip port opening 14 of the sleeve 11 may be of variable length from the proximal end housing 17. In preferred embodiments, the length of the sleeve 11 covers the entire length of the elongated shaft 12 of the scope from the proximal end housing 17 to distal tip port opening 14. Likewise, bold, wavy lines to the left of the proximal end housing 17 suggest a variability of length of sleeve from the proximal end housing 17 to the proximal base of the scope 13. In preferred embodiments, the proximal end housing 17—encasing the motor output 17a and actuator gear 17b—may be situated close to the proximal base of the scope 13. Such a configuration may allow the clinician to control the functions of the endoscope, while still being able to manipulate the finger-led controls 19 disposed on any one of a surface of the proximal end housing 17. The finger-led controls 19, shown on the top surface of the proximal end housing 17 in FIG. 1, allows the clinicians to control axial rotation of the sleeve 11. The close proximity of housing 17 with base 13, may allow the clinician to have the convenience to control any one of the channels of the scope, while simultaneously controlling axial rotation of the sleeve 11. Similarly, the close proximity of base 13 to housing 17, may allow a clinician to visualize a body lumen through a fiber-optic channel/eye-piece and control axial rotation of the sleeve during forward propulsion through the said lumen. In other embodiments, a foot-led control remotely situated from the apparatus may control axial rotation of the sleeve 11. In yet other embodiments, a hand-held control proximally or remotely situated from the apparatus may control axial rotation of the sleeve 11.

While not shown in FIG. 1, each lumen or working channel of the scope may be coupled to its dedicated control for control of agent, suction, loop, and, or image capture. The sleeve apparatus may be slidably disposed over a tubular member of any one of a flexible or rigid endoscope, wherein the apparatus is configured to operate under any one of, or combination of, a control circuitry, control module, motor output 17a/actuator gear 17b, of any one of, or combination of the apparatus, and, or the endoscope. In integrated embodiments, the apparatus is integrated wholly with the endoscope, including the control commands. In other words, a physician may use the interface of the endoscope in order to control the axial rotation of the sleeve apparatus. In other embodiments, control commands will be shared, wherein a physician may interface with both the endoscope and sleeve apparatus in order to control axial rotation of the sleeve apparatus. In preferred embodiments, a physician may strictly interface with the apparatus via the finger-led control disposed on a top surface of the housing to control axial rotation of the sleeve apparatus.

The sleeve 11 may be slid over the elongated shaft 12 of the endoscope with the distal tip port opening 16 aligned to the distal tip 14 of the endoscope. The proximal end of the sleeve 11 may have slits 11a which are to be fitted into the prongs 18a of the sleeve-actuator junction seal 18. The fitting may be done by first assembling the proximal end housing 17 over the proximal base 13 of the scope, then sliding over the sleeve 11 and fitting the slits 11a of the sleeve 11 onto the prongs 18a of the sleeve-actuator junction seal 18. The proximal end housing 17 may be fitted over the base 13 by any of Snap-on or clip-on mechanism. Alternatively, the sleeve 11 may be slid first and then the proximal end housing 17 may be fitted over the proximal base 13 of the scope and then fitted via the slit 11a/prongs 18a of the sleeve-actuator junction seal 18. In yet other embodiments, the sleeve 11 is pre-fitted onto the proximal end housing 17 and then jointly slid over the elongated shaft 12, such that the distal tip port opening 16 of the sleeve 11 is aligned to the distal tip 14 of the scope, and the proximal end housing 17 is adjacent to the proximal base 13 of the scope.

Figure 2:
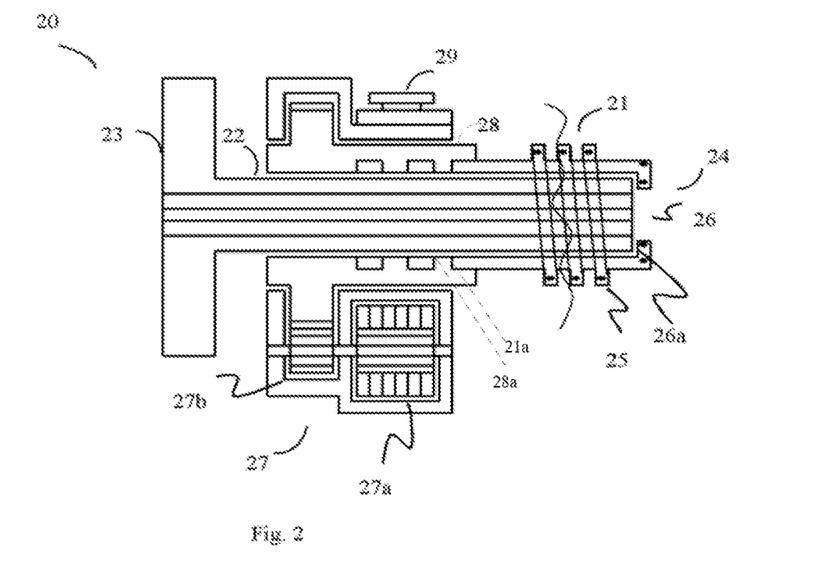
FIG. 2 is a close-up view of the sleeve-actuator junction seal of the apparatus according to an aspect of the invention.
Figure 3:
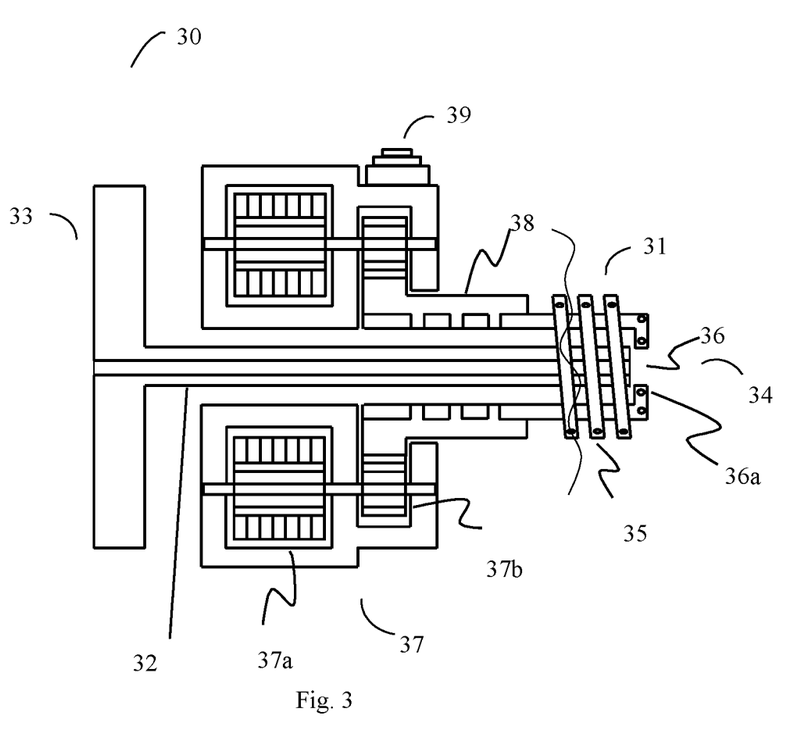
FIG. 3 is a close up view of the dual motor configuration of the apparatus according to an aspect of the invention.
Figure 4:
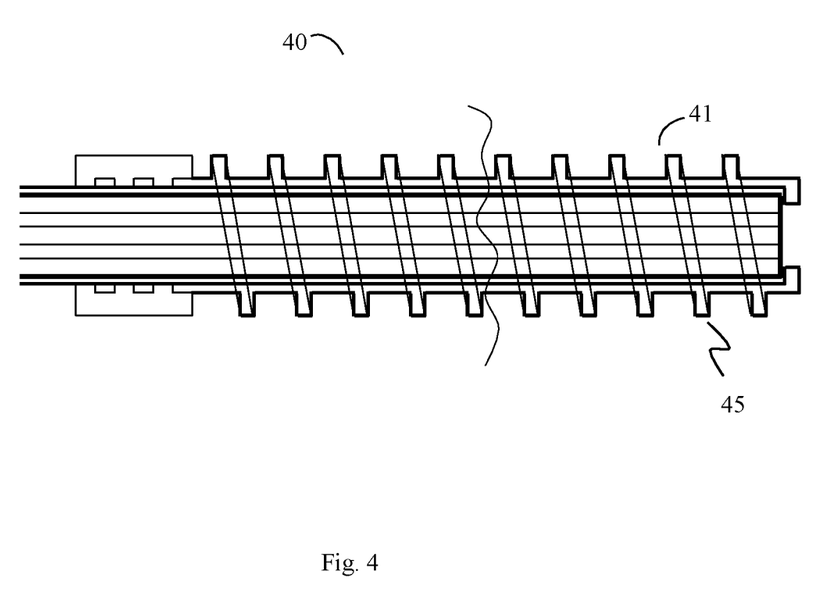
FIG. 4 is a close-up view of the helical threading of the apparatus according to an aspect of the invention.
Figure 5:
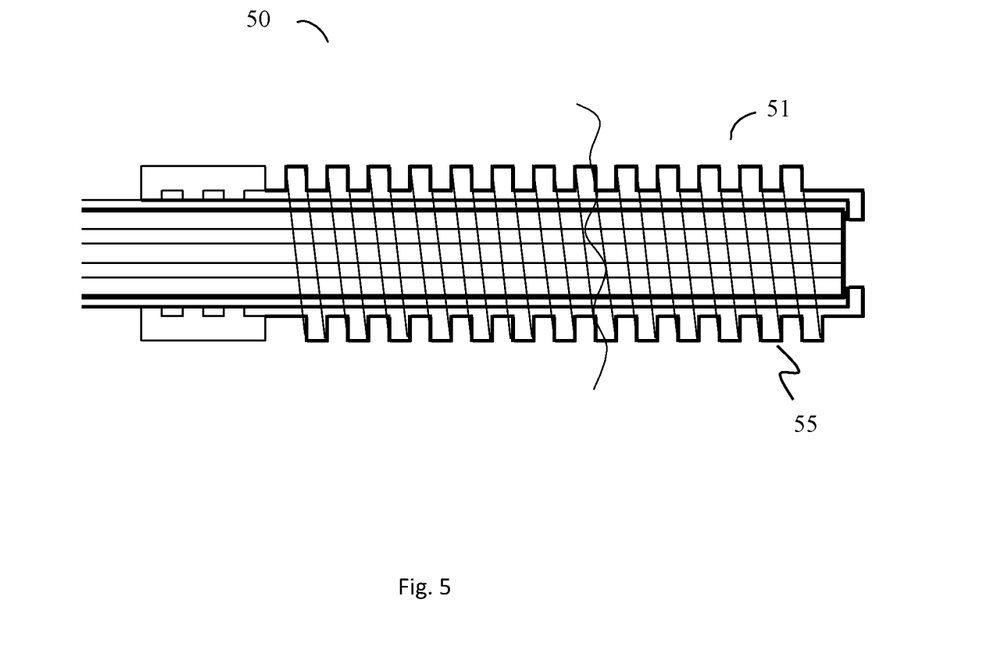
FIG. 5 is a close-up view of the helical threading of the apparatus according to an aspect of the invention.
Figure 6:
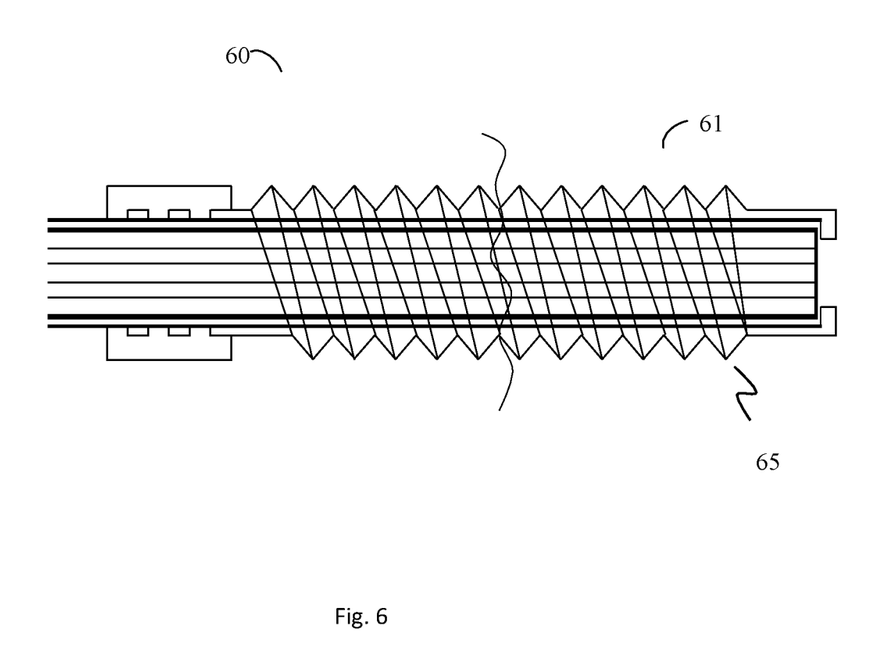
FIG. 6 is a close-up view of the helical threading of the apparatus according to an aspect of the invention.
Figure 7:
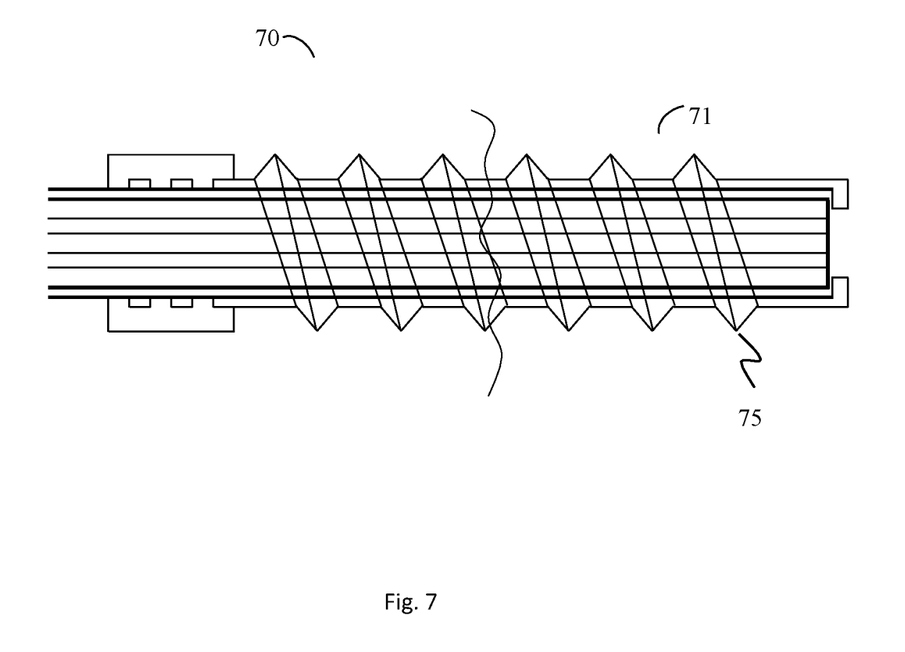
FIG. 7 is a close-up view of the helical threading of the apparatus according to an aspect of the invention.

Now in reference to FIGS. 2 and 3. FIG. 2 depicts a close-up view of the proximal end housing of the apparatus, more particularly of the single motor configuration. FIG. 3, likewise, depicts a close-up view of the proximal end housing of the apparatus—though depicting a dual motor configuration. As FIGS. 2 and 3 show, the proximal end housing 27, 37 comprises: at least one motor 27a, 37a coupled to at least one actuator gear 27b, 37b, whereby said actuator 27b, 37b is in operable communication to the rotatable sleeve 21, 31 via a sleeve-actuator junction seal 28, 38; a finger-led control 29, 39 disposed on a surface of the proximal end housing 27, 37 and operably coupled to the motor 27a, 37a and, or actuator gear 27b, 37b for triggering rotational force. Furthermore, the rotational force caused by the motor 27a, 37a and, or actuator gear 27b, 37b drives axial rotation of the rotatable sleeve 21, 31 over the elongated shaft member of the endoscope via the sleeve-actuator junction seal 28, 38, and thereby allowing for forward propulsion of the endoscope with epithelial tearing risk mitigation.

As depicted in FIG. 2 and FIG. 3, the proximal end housing 27, 37 may have at least one finger-led control 29, 39 coupled to at least one actuator 27b, 37b, whereby the finger-led control 29, 39 disposed on a surface of the proximal end housing 27, 37 and operably coupled to the motor 27a, 37a and, or actuator gear 27b, 37b for triggering rotational force. Subsequently, the rotational force caused by the motor 27a, 37a and, or actuator gear 27b, 37b drives axial rotation of the rotatable sleeve 21, 31 over the elongated shaft member 22, 32 of the endoscope via the sleeve-actuator junction seal 28, 38, and thereby allowing for forward propulsion of the endoscope with epithelial tearing risk mitigation. Alternatively, the rotational force and subsequent sleeve 21, 31 rotation may be triggered by a remote foot pedal control, or even by a hand-held remote control device.

The sleeve-actuator junction seal 28, 38 gear is opposably coupled to at least one motor-coupled actuator gear 27b, 37b resulting in counter-directional rotation of said opposable gears for causing rotation of the rotatable sleeve 21, 31 over the elongated shaft member 22, 32. The proximal end housing 27, 37 encases the at least one actuator gear 27b, 37b coupled to the at least one motor 27a, 37a, whereby a rod may be rotatably coupled to the motor 27a, 37a and axially disposed through the actuator gear 27b, 37b. In other embodiments, the motor 27a, 37a is in communication with the actuator gear 27b, 37b, without an axial rod disposed through the actuator gear 27b, 37b. Communication between motor 27a, 37a and actuator gear 27b, 37b may be adjacent to another and rotationally synced. Alternatively, communication between motor 27a, 37a and actuator gear 27b, 37b may be by direct gear-gear contact to one another and rotationally counter-synced.

In a preferred embodiment, the sleeve-actuator junction seal 28, 38 couples the rotatable sleeve 21, 31 by prongs 18a disposed on a top surface of the seal 28, 38 to lock into complementary dimensioned wells or slits 11a on a top surface of the sleeve 21, 31. This prong-slit locking mechanism, is simple and allows a clinician to easily lock the sleeve 21, 31 to seal 28, 38 once after the sleeve 21, 31 has been slid over the elongated shaft member 22, 32 and the proximal end housing 27, 37 with seal 28, 38 prongs 18a may be fitted through the sleeve 21, 31 slits 11a first and then the unified apparatus may be slid over the elongated shaft member 22, 32 of the endoscope until it reaches the appropriate location of the proximal base 23, 33 of the endoscope. Due to the elasticity of the polymer material of the sleeve 21, 31, fitting over the prongs 18a of the seal 28, 38 is secure, without the need of any additional locking mechanism. However, in some embodiments, a locking means, such as a snap attachment, between the sleeve 21, 31 and seal 28, 38 may be provided.

While not shown in FIG. 2 or 3, the proximal end housing 27, 37 may be disposed with a finger-led control 29, 39 on a top housing for causing rotational output. In some embodiments, however, the top housing may additionally comprise of endoscopic channel controls. This may allow a clinician to have an integrated interface for sleeve 21, 31 rotation, along with a plurality of endoscopic channel controls: visualization, looping, agent deployment, and, or suction, etc. An integrated interface display or interface display dedicated strictly for sleeve 21, 31 rotation may be provided. In either case, the front or top wall of the proximal end housing 27, 37 may include a user interface display, wherein the user interface may be integrated as a built-in console display.

Although not shown in FIG. 2 or 3, a built-in console display disposed on a front or top end of the proximal end housing 27, 37 may authenticate a clinician/patient by requiring an identification code that may be inputted from the display, as a means for verifying the clinician/patient. Alternate embodiments may involve a built-in console display authenticating a clinician/patient by any form of short-range communication standard. For instance, in authenticating a clinician/patient, an authentication module may be further caused to recognize the endoscope/sleeve apparatus at a particular interventional procedure console disposed with a unique short-range communication tag. The module may identify and authenticate the particular console and scope/sleeve by recognizing the unique tag, and then, authenticate the clinician/patient by identifying the scope/sleeve device located at the particular procedure console. The unique, short-range tag may be a NFC tag, RFID chip, bluetooth, ZigBee, or any short-range or long-range communication protocol standard.

While also not shown in FIG. 2 or 3, embodiments may include the addition of a remote server to provide for back-end functionality and support. The server may be situated adjacent or remotely from the system and connected to each system via a communication network. In one embodiment, the server may be used to support verification or authentication of a clinician and, or patient. Other embodiments may include a remote server that is configured to provide a contextually-aware patient health engine, which may access real-time data and at least one patient contextual information to cause the processor to display a suggested routine or treatment on the built-in console display. The display may include a display page for receiving a request for real-time upload and, or back-end analytics/provisioning. Such provisioning may inform and guide a clinician with real-time information and pertinent contextual information.

Now in reference to FIGS. 4, 5, 6, and 7. FIGS. 4-7 depict a close-up view of the variations of helical screw threading disposed on the outer surface of the sleeve. The helical screw threading 45, 55, 65, 75 may be disposed on the outer surface of the sleeve 41, 51, 61, 71 and radially extending to a distal tip for endoscopic propulsion. The helical screw threading 45, 55, 65, 75 is primarily a ridge wrapped around the sleeve 41, 51, 61, 71 with varying lead, shape, space, and angle characteristics. The helical threading 45, 55, 65, 75 is intended to further engage the surrounding medium of any body lumen and facilitate forward propulsion through the conversion of rotary to linear motion. Variations in the lead, shape, space, and angle characteristics may affect multiple parameters related to the conversion of rotary motion to linear motion in any given medium: torque, pull, slip, etc.

For instance, in a highly looped medium, such as an intestine, a helical threading 45, 55, 65, 75 with a perpendicular angle characteristic with low-spaced or contiguous threading (FIG. 5) may be optimal for controlled propulsion, while minimizing slippage and, or tearing an epithelial lining. Conversely, a helical threading 45, 55, 65, 75 with an angular characteristic with spaced threading (FIG. 7) may be optimal for propulsion through largely a linear and unobstructed medium.

The helical screw thread 45, 55, 65, 75 lead may be optimized in order to maintain controlled propulsion, while preventing slippage even when linear force is being applied by the physician during the endoscopic procedure. Slippage may exacerbate tearing of the epithelial lining, so slippage prevention is paramount. The lead may be optimized for the dimensions of the scope and for the specific characteristics of the medium. The lead distance of the helical threading may be any one of a distance between 1 mm to 50 mm, depending on the specific characteristics of the medium.

The threading 45, 55, 65, 75 may have a thread form having any one of a v-shaped, triangular, square, and trapezoidal thread form. Thread form may be complementary to the specific characteristics of the medium. The dimensions of any one of the thread form result in a far more streamlined sleeve, compared to the currently existing balloon/belt assemblies circumventing sleeve or scope shafts. Additionally, the handedness of the helical screw threading 45, 55, 65, 75 may vary between right-handedness or left-handedness. Again, the handedness may be chosen based on the characteristics of the medium.

In alternative embodiments, the sleeve 41, 51, 61, 71 may further comprise a collapsible and extendable sleeve backbone disposed on the inner surface/crest of the groove of the screws of the sleeve 41, 51, 61, 71, extending from a proximal base and radially extending to a distal tip for uniform rotation of the sleeve 41, 51, 61, 71. This collapsible back-bone may further reinforce the sleeve 41, 51, 61, 71 for uniform rotation and prevent snagging of the sleeve 41, 51, 61, 71 during rotation. The back-bone has minimal protrusion and does not impede the linear propulsion of the apparatus during engagement with the medium. The backbone embodiment and the preferred embodiments with just the helical screw threading 45, 55, 65, 75 have overall dimensions far less protrusive than the extant balloon/belt assemblies circumventing sleeve and, or scope shafts.

Also disclosed is a method for mitigating propulsion-related epithelial tearing, the method comprising the steps of: (1) threading an outer surface of a rotatable sleeve encasing an elongated shaft member of an endoscope, from a proximal base of the endoscope and radially extending to a distal tip of the endoscope; (2) coupling at least one motor to at least one actuator gear, whereby said actuator gear is in operable communication to the rotatable sleeve via a sleeve-actuator junction seal; and finally, (3) triggering rotational force by a finger-led control disposed on a surface of the proximal end housing and operably coupled to the motor and, or actuator gear; and wherein the rotational force caused by the motor and, or actuator gear drives axial rotation of the rotatable sleeve over the elongated shaft member of the endoscope via the sleeve-actuator junction seal, and thereby allowing for forward propulsion of the endoscope with epithelial tearing risk mitigation.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with variations from the illustrations. Thus, embodiments of the invention should not be construed as limited to the particular shapes of regions illustrated herein but are to include deviations in shape and form. Thus, the regions illustrated in the figures are schematic in nature and their shapes are not intended to illustrate the actual shape of a region of a device and are not intended to limit the scope of the invention.

Unless otherwise defined, all terms used in disclosing embodiments of the invention, including technical and scientific terms, have the same meaning as commonly understood by one of ordinary skill in the art to which this invention belongs, and are not necessarily limited to the specific definitions known at the time of the present invention being described. Accordingly, these terms can include equivalent terms that are created after such time. It will be further understood that terms, such as those defined in commonly used dictionaries, should be interpreted as having a meaning that is consistent with their meaning in the present specification and in the context of the relevant art and will not be interpreted in an idealized or overly formal sense unless expressly so defined herein. All publications, patent applications, patents, and other references mentioned herein are incorporated by reference in their entirety.

In the following description, for purposes of explanation, numerous specific details are set forth in order to provide a thorough understanding of the invention. It will be apparent, however, to one skilled in the art that the invention can be practiced without some specific details. Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments. Although a few exemplary embodiments of the present disclosure have been shown and described, the present disclosure is not limited to the described exemplary embodiments. Instead, it would be appreciated by those skilled in the art that changes may be made to these exemplary embodiments without departing from the principles and spirit of the present disclosure, the scope of which is defined by the claims and their equivalents.

It will be understood that when a layer is referred to as being "disposed on top of" another layer, it can be directly on the other layer or intervening layers may also be present. In contrast, when a layer is referred to as "communicating with" another layer, there are no intervening layers present. Similarly, it will be understood that when a layer is referred to as being "below" another layer, it can be directly under the other layer or intervening layers may also be present.

It will also be understood that, although the terms first, second, etc. may be used herein to describe various elements, these elements should not be limited by these terms. These terms are only used to distinguish one element from another. For example, a first layer could be termed a second layer, and, similarly, a second layer could be termed a first layer, without departing from the scope of the present invention.

I claim:

1. An endoscopic sleeve apparatus for mitigating propulsion-related epithelial tearing and tissue damage, said apparatus comprising:
    an elastomeric, pliable, and rotatable sleeve for encasing an elongated shaft member of an endoscope, the sleeve comprising wells or slits through a proximal end of the sleeve;
    any one of a right-turn or left-turn helical threading disposed on an outer surface of the sleeve from a proximal base of the endoscope and radially extending to a distal tip of the endoscope;
    a distal tip port opening configured for allowing at least one channel and/or lumen axially disposed within the elongated shaft member of the endoscope to be engaged to the distal tip port opening for release and/or capture of any agent;

a housing at the proximal end of the sleeve;

a sleeve-actuator junction seal comprising prongs on a surface of the sleeve-actuator junction seal facing the proximal end of the sleeve;

at least one motor coupled to at least one actuator gear contained within the housing, whereby said actuator gear is in operable communication to the sleeve via the sleeve-actuator junction seal;

a prong-well locking mechanism to securely attach the elastic sleeve to the sleeve actuator junction seal to avoid displacement of the sleeve from the shaft member during operation, wherein prongs disposed on the surface of the seal facing the sleeve, securely fit into complementary dimensioned wells or slits on the proximal end of the sleeve;

a finger-led control disposed on the housing and operably coupled to the motor and/or actuator gear for triggering axial rotational force; and wherein the axial rotational force caused by the motor via the actuator gear drives axial rotation of the sleeve over the elongated shaft member of the endoscope via the sleeve-actuator junction seal, and thereby allowing for forward and reverse propulsion of the endoscope through a lumen.

2. The apparatus of claim 1, further comprising an additional motor-coupled actuator gear coupled to the sleeve-actuator junction seal, wherein the additional motor-coupled actuator gear is opposably paired across the sleeve-actuator junction seal.

3. The apparatus of claim 1, wherein the sleeve-actuator junction seal comprises a gear opposably coupled to at least one motor-coupled actuator gear resulting in counter-directional rotation of said opposably-coupled gears for causing rotation of the sleeve.

4. The apparatus of claim 1, wherein the housing encases the at least one actuator gear, wherein the one actuator gear is mechanically coupled to one motor.

5. The apparatus of claim 1, wherein the housing attaches to the endoscope by any one of a snap on to the proximal base of the endoscope and/or is slidably disposed over the elongated shaft member from a distal end to rest at the proximal base of the endoscope.

6. The apparatus of claim 1, further comprising a collapsible and extendable sleeve back-bone disposed on the inner surface of the sleeve from a proximal base and radially or linearly extending to a distal tip for uniform rotation of the sleeve.

7. The apparatus of claim 1, wherein the helical threading disposed on the outer surface of the sleeve and radially extending to a distal tip for endoscopic propulsion, said threading having any one of a v-shaped, triangular, square, and trapezoidal thread form.

8. The apparatus of claim 1, wherein the housing and/or the sleeve is water-proof and sterilization-grade.

9. An endoscopic sleeve apparatus for mitigating propulsion-related epithelial tearing, said apparatus comprising:

an elastomeric, pliable, and rotatable sleeve for encasing an elongated shaft member of an endoscope and comprising wells or slits through a surface of a proximal end of the sleeve;

any one of a right-turn or left-turn helical threading disposed on an outer surface of said sleeve, from a proximal base of the endoscope and radially extending to a distal tip of the endoscope;

a lip or overhang through a lumen of the sleeve disposed on a distal tip of the sleeve to prevent the shaft member of the endoscope from sliding out of the distal tip of the sleeve;

a proximal end housing comprising at least one motor coupled to at least one actuator gear, whereby said actuator gear is in operable communication to the sleeve;

a sleeve-actuator junction seal comprising prongs on an inner surface of the sleeve-actuator junction seal, wherein said seal enables the actuator gear to be in operable communication to the sleeve;

said prongs disposed on the inner surface of the junction seal facing the proximal end of the sleeve, said proximal end of the sleeve comprising wells or slits complimentarily dimensioned to the prongs, wherein during ordinary operation, the sleeve is attachable to and detachable from the junction seal, and, during attachment of the sleeve to the seal, the prongs are fitted into the wells to securely lock the sleeve to the junction seal to avoid displacement during operation; and a rotational force caused by the motor via the actuator gear drives axial rotation of the rotatable sleeve over the elongated shaft member of the endoscope via the sleeve-actuator junction seal, and thereby allowing for forward and reverse propulsion of the shaft member of the endoscope with epithelial tearing risk mitigation, while avoiding displacement of the sleeve and avoiding the shaft member of the endoscope from sliding out of the distal tip of the sleeve.

10. The apparatus of claim 9, further comprising an additional motor-coupled actuator gear coupled to the sleeve-actuator junction seal, wherein the additional motor-coupled actuator gear is opposably paired across the sleeve-actuator junction seal.

11. The apparatus of claim 9, wherein the sleeve-actuator junction seal comprises a gear opposably coupled to at least one motor-coupled actuator gear resulting in counter-directional rotation of said opposably coupled gears for causing axial rotation of the sleeve over the elongated shaft member.

12. The apparatus of claim 9, wherein the housing encases the at least one actuator gear, wherein the at least one actuator gear is mechanically coupled to the at least one motor.

13. The apparatus of claim 9, wherein the housing attaches to the endoscope by any one of a snap on to the proximal base of the endoscope and/or is slidably disposed over the distal end of the elongated shaft member to rest at the proximal base of the endoscope.

14. The apparatus of claim 9, further comprising a collapsible and extendable sleeve back-bone disposed on the inner surface of the sleeve from a proximal base and linearly and, or radially extending to a distal tip for uniform rotation of the sleeve.

15. The apparatus of claim 9, wherein the helical threading disposed on the outer surface of the sleeve and radially extending to a distal tip for endoscopic propulsion, said threading having any one of a v-shaped, triangular, square, and trapezoidal thread form.

16. The apparatus of claim 9, wherein the housing and/or the sleeve is at least one of water-proof and/or sterilization-grade.

* * * * *